(12) United States Patent
Pappalardo et al.

(10) Patent No.: US 10,914,647 B2
(45) Date of Patent: Feb. 9, 2021

(54) CAPACITIVE PRESSURE SENSOR FOR MONITORING CONSTRUCTION STRUCTURES, PARTICULARLY MADE OF CONCRETE

(71) Applicant: STMicroelectronics S.r.l., Agrate Brianza (IT)

(72) Inventors: Francesco Pappalardo, Paternò (IT); Agatino Pennisi, Catania (IT); Elio Guidetti, Montano Lucino (IT); Angelo Doriani, Misterbianco (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 419 days.

(21) Appl. No.: 16/023,918

(22) Filed: Jun. 29, 2018

(65) Prior Publication Data

US 2019/0011320 A1  Jan. 10, 2019

(30) Foreign Application Priority Data

Jul. 5, 2017 (IT) .......................... 102017000073763

(51) Int. Cl.
*G01L 1/00* (2006.01)
*G01L 9/00* (2006.01)
(Continued)

(52) U.S. Cl.
CPC ............ *G01L 9/0075* (2013.01); *G01L 1/142* (2013.01); *G01L 19/0023* (2013.01); *G01M 5/0083* (2013.01); *G01N 33/383* (2013.01)

(58) Field of Classification Search
CPC ..... G01L 9/0075; G01L 1/142; G01L 19/0023
See application file for complete search history.

(56) References Cited

U.S. PATENT DOCUMENTS

| 4,184,189 A | 1/1980 | Davis et al. |
| 6,450,039 B1 * | 9/2002 | Masuda ............... G01L 19/0069 |
| | | 73/756 |

(Continued)

FOREIGN PATENT DOCUMENTS

| CN | 101846562 A | 9/2010 |
| CN | 102928133 A | 2/2013 |

(Continued)

*Primary Examiner* — Jamel E Williams
(74) *Attorney, Agent, or Firm* — Seed IP Law Group LLP

(57) ABSTRACT

A capacitive sensor for monitoring stresses acting in a construction structure and having a multi-layer structure provided with an upper conductive layer defining an upper outer surface of the sensor. A lower conductive layer defines a lower outer surface. At least a first structural layer of insulating material is in contact with the upper conductive layer and at least a second structural layer of insulating material is in contact with the lower conductive layer. At least a first plate layer of conductive material and at least a second plate layer, of conductive material, and at least one dielectric layer is interposed between the first plate layer and the second plate layer to define at least one detection capacitor inside the multi-layer structure of the sensor. The upper and lower conductive layers jointly defining an electromagnetic screen for screening the detection capacitor against electromagnetic interference originating from outside the capacitive sensor.

21 Claims, 10 Drawing Sheets

(51) Int. Cl.
    *G01M 5/00*    (2006.01)
    *G01L 1/14*    (2006.01)
    *G01L 19/00*    (2006.01)
    *G01N 33/38*    (2006.01)

(56) References Cited

U.S. PATENT DOCUMENTS

| | | | |
|---|---|---|---|
| 8,997,588 B2 | 4/2015 | Taylor | |
| 9,791,339 B2* | 10/2017 | Mullis | G01L 21/00 |
| 2012/0017691 A1* | 1/2012 | Ishihara | G01L 9/0075 |
| | | | 73/724 |
| 2012/0206147 A1* | 8/2012 | Sim | G01K 7/34 |
| | | | 324/457 |
| 2012/0247216 A1* | 10/2012 | Ishihara | G01L 9/0072 |
| | | | 73/708 |
| 2014/0150559 A1* | 6/2014 | Ishihara | G01L 19/147 |
| | | | 73/718 |
| 2014/0174204 A1 | 6/2014 | Chen et al. | |
| 2014/0182386 A1* | 7/2014 | Ishihara | G01L 19/0627 |
| | | | 73/754 |
| 2015/0040674 A1* | 2/2015 | Ishihara | G01L 19/0636 |
| | | | 73/724 |
| 2017/0241855 A1* | 8/2017 | Sooriakumar | H05K 3/4038 |
| 2017/0248487 A1* | 8/2017 | Ishihara | C23C 16/52 |
| 2018/0238756 A1* | 8/2018 | Ishihara | G01L 19/0636 |
| 2018/0238757 A1* | 8/2018 | Soeda | G01L 13/025 |
| 2018/0259409 A1* | 9/2018 | Sekine | G01L 9/125 |
| 2019/0226936 A1* | 7/2019 | Ishihara | G01L 27/007 |
| 2019/0292042 A1* | 9/2019 | Liu | H01L 43/02 |

FOREIGN PATENT DOCUMENTS

| | | |
|---|---|---|
| CN | 105424231 A | 3/2016 |
| CN | 106153219 A | 11/2016 |
| TW | 201425889 A | 7/2014 |
| WO | 2017/033036 A1 | 3/2017 |

* cited by examiner

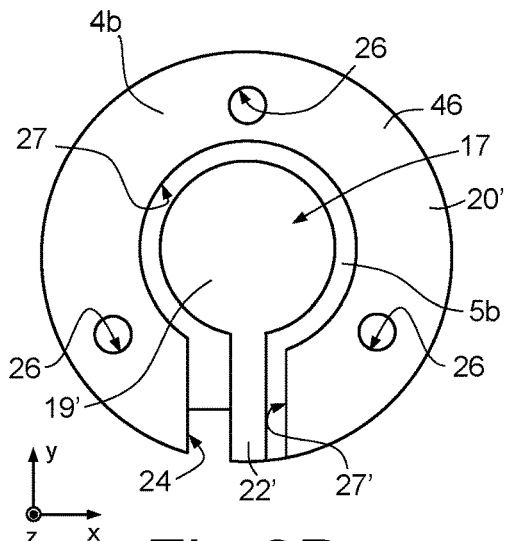
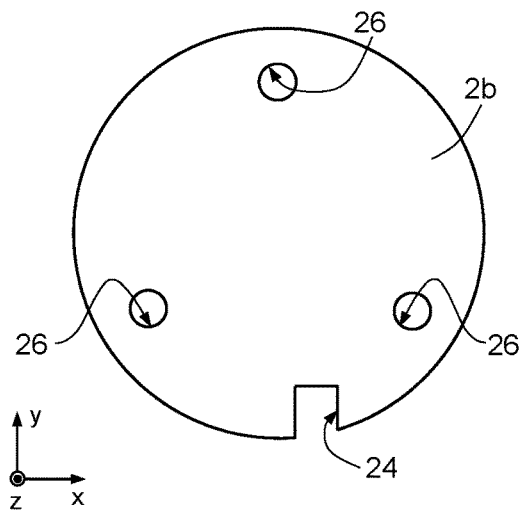
Fig.8D     Fig.8E
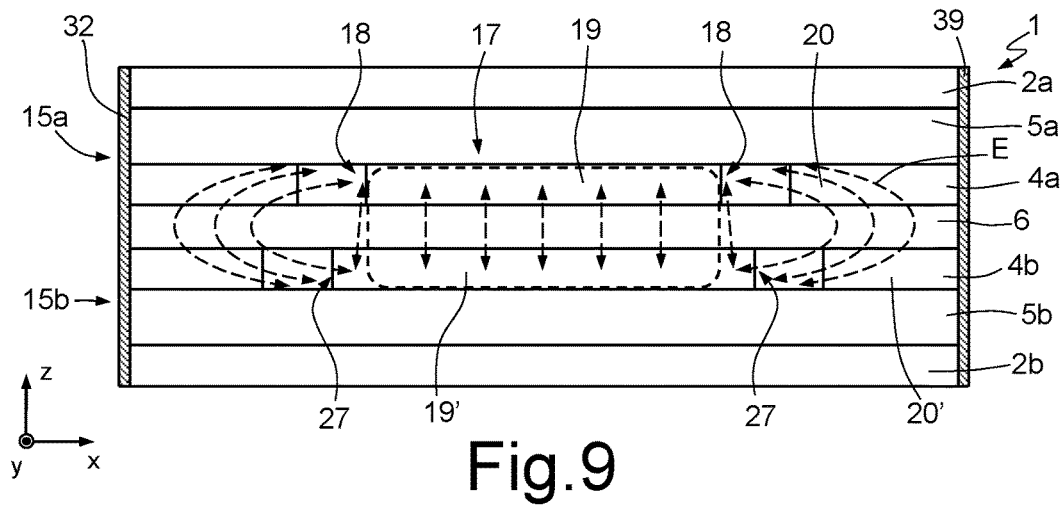
Fig.9
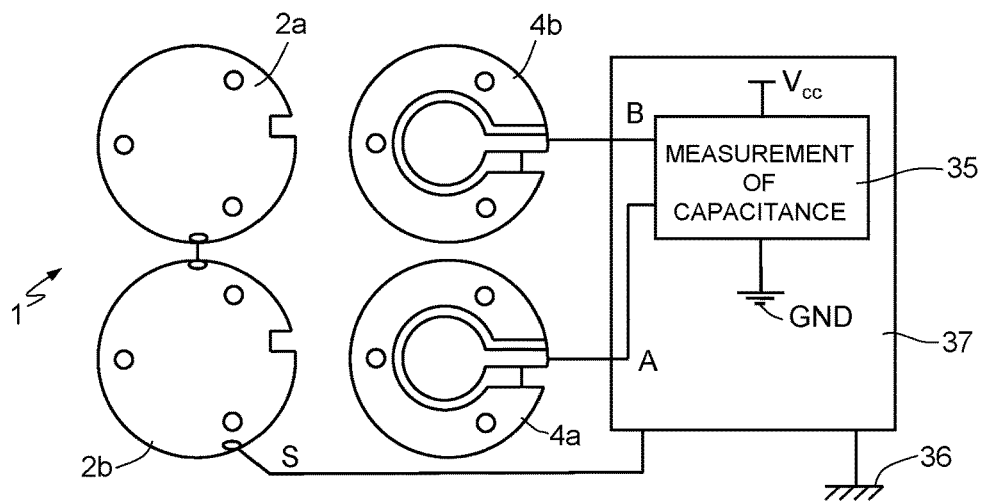
Fig.10A

CAPACITIVE PRESSURE SENSOR FOR MONITORING CONSTRUCTION STRUCTURES, PARTICULARLY MADE OF CONCRETE

BACKGROUND

Technical Field

The present solution relates to a capacitive pressure sensor for monitoring the state of construction structures such as buildings, infrastructure and the like.

Description of the Related Art

Reference is made below to construction structures made of concrete as the preferred area of application. However, the present solution is applicable in principle to structures or parts of structures of various types, particularly those made from materials which are partially liquid or fluid at the time of manufacture or production and intended to harden subsequently, where there is a desire to monitor the state of health and stress of these structures over time.

As is known, it has been considered necessary to monitor and evaluate over time the state of health of structures produced by the building industry, such as tunnels, bridges or flyovers, with the aim of preventing the occurrence of fractures and accidents. In particular, it is necessary to monitor the loads supported, and any extraordinary stresses, forces or strain that may act on the material of which the structure is composed.

Some of the current techniques of non-destructive evaluation (NDE) use sensors, fixed externally to the structure to be monitored, which, operating on mechanical, optical or magnetic principles for example, indirectly measure the stresses acting on the structure concerned by correlation with other measurable variables (inclination, deformation, etc.). For example, the use of extensometers, mounted externally on the structures to be monitored, has been proposed for making indirect measurements of deformation.

As a rule, however, these sensors are bulky, costly and subject to error. Complex electronic interfaces are also usually needed for processing the information acquired and for correlating it with the forces and stresses to be monitored.

Other known solutions provide for the use of suitable sensors, for example ceramic sensors, embedded in the structure to be monitored. In this case, however, if the sensors are not adequately protected, they are frequently subject to humidity and/or other factors which falsify their results and/or reduce their operational life. Moreover, the positioning of these sensors is often critical, and they may, in particular, become partially detached from the material of the structure to be monitored (a process known as delamination), for example owing to the presence of sand, grit or air bubbles trapped in a concrete structure, which interfere with the sensors.

In general, the large-scale use of sensors applied to buildings and civil engineering structures requires the development of innovative sensors capable of meeting one or more of the following requirements: high accuracy; high robustness; low cost; high immunity to electromagnetic interference that might falsify the detection results; simplicity and stability of positioning; simplicity of operation; and good surface adhesion to the structure to be monitored.

In particular, as regards the requirement for immunity to electromagnetic interference, it is found that, in the environment in which the sensors carry out monitoring, especially during the construction of the structure to be monitored, electrical machines which generate high magnetic fields when in use are typically present, including, for example, excavating machines, machines for extracting material, hydraulic pumps, etc.

BRIEF SUMMARY

The present disclosure provides a sensor for monitoring construction structures which overcomes at least some of the drawbacks of the prior art and can meet the needs and requirements of the industry.

According to the present disclosure, a capacitive pressure sensor, as defined in the appended claims, is provided.

BRIEF DESCRIPTION OF THE SEVERAL VIEWS OF THE DRAWINGS

To enable the present disclosure to be understood more readily, preferred embodiments thereof will now be described, purely by way of non-limiting example, with reference to the attached drawings, in which:

FIG. 8D is a layout view of a second plate layer of the sensor of FIG. 8A;

FIG. 8E is a layout view of a lower metal layer of the sensor of FIG. 8A;

FIG. 9 is a cross-sectional view of the sensor of FIG. 8A showing electric field lines associated with a corresponding detection capacitor;

FIGS. 10A-10B are schematic representations of electrical connections between capacitive pressure sensors according to embodiments of the present disclosure and a corresponding measurement circuit;

DETAILED DESCRIPTION

The present applicant has, in the first place, found that a capacitive sensor having flat parallel sheets or plates (known as a PPCS, for Parallel Plate Capacitor Sensor) may have characteristics such that it can meet the requirements for detection of the stresses within a construction structure, particularly a concrete structure, and can offer high sensitivity to small relative movements between the plates (due to the stresses to be monitored), the possibility of being coupled to a standard electronic interface, high configurability for adaptation to different detection requirements, and high adhesion to the material of the structure to be monitored, minimizing the risk of detachment and the possibility of interference with air bubbles, sand, grit or other rough areas in the structure.

As will now be described in detail, the present solution provides technical production arrangements to ensure that the flat parallel plate capacitive sensor operates correctly as an optimized pressure sensor in the structure to be monitored, particularly in a concrete structure.

Figure 1A:
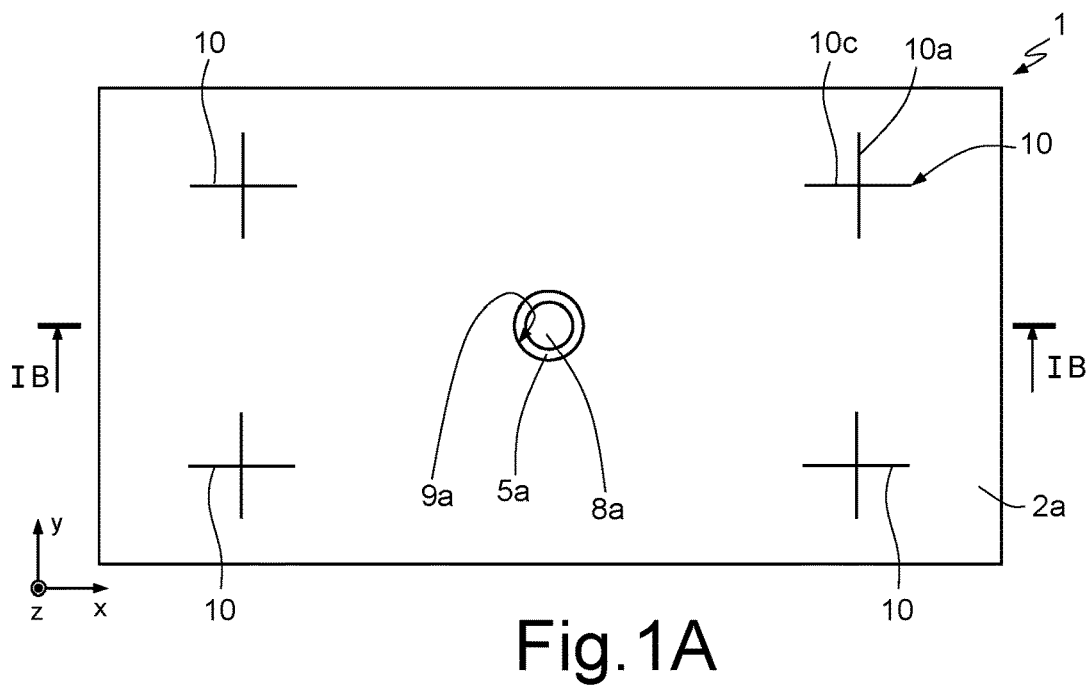
FIG. 1A is a schematic representation, in plan view, of a capacitive pressure sensor according to an embodiment of the present solution.
Figure 1B:
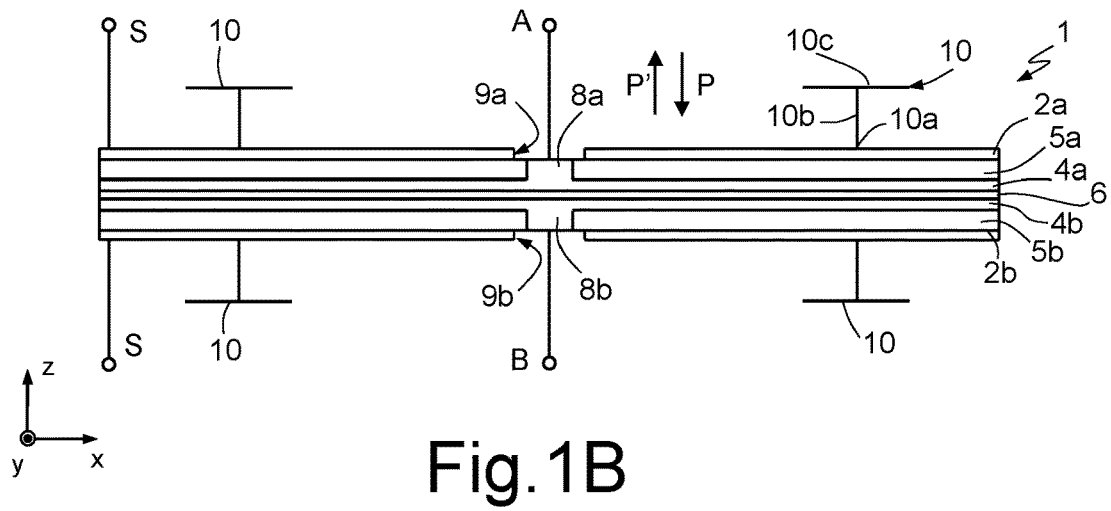
FIG. 1B is a cross-sectional view of the sensor of FIG. 1A.

FIGS. 1A and 1B show, in a plan view and in a cross section respectively, the general detection structure of a capacitive pressure sensor according to embodiments of the present solution, of the flat parallel plate type, which can be used to monitor the state of a concrete structure (not shown) when inserted into the structure concerned. As discussed below, the structure is formed by the techniques used for semiconductor materials, particularly for printed circuit boards (PCB).

The capacitive sensor, indicated in a general way by 1, comprises a first outer metal layer 2a, made for example of copper or other conductive material, having a planar extension in a horizontal plane xy, and a second outer metal layer 2b, also made, for example, of copper or other conductive material and having a planar extension in the horizontal plane xy. The first outer metal layer 2a may be considered as an upper metal layer (and is referred to as such below), and the second outer metal layer 2b may be considered as a lower metal layer (and is referred to as such below), relative to the direction of a vertical axis z orthogonal to the horizontal plane xy.

The capacitive sensor 1 further comprises, between the upper metal layer 2a and the lower metal layer 2b, a first plate layer 4a, of copper for example, having a planar extension in the horizontal plane xy. A first structural layer 5a, of insulating material, for example glass ceramic, Vetronite or FR-4 (a composite material consisting of glass fibers joined together by an epoxy resin), interposed in contact between the upper metal layer 2a and the first plate layer 4a. A second plate layer 4b, also of copper for example, having a planar extension in the horizontal plane xy, and a second structural layer 5b of insulating material, which for example is also made of glass ceramic, Vetronite or FR-4, is interposed in contact between the lower metal layer 2b and the second plate layer 4b. The capacitive sensor 1 further comprises a dielectric layer 6, having a planar extension in the horizontal plane xy and interposed between the first and the second plate layer 4a, 4b so as to form a detection capacitor C with flat parallel faces, the plates of which are defined by the first and second plate layers 4a, 4b.

Thus the capacitive sensor 1 has a multi-layer structure, with layers stacked in the direction of the vertical axis z, which, by means of the first and second plate layer 4a, 4b and the interposed dielectric layer 6, defines within itself the detection capacitor C.

The capacitive sensor 1 further comprises a first contact element 8a, made of conductive material, for example copper, which electrically contacts the first plate layer 4a, and in particular the plate of the detection capacitor C defined by the first plate layer 4a.

In the illustrated example, the first contact element 8a extends vertically through the whole thickness of the first structural layer 5a, contacting the first plate layer 4a. A first contact opening 9a is formed through the upper metal layer 2a, at the position of the first contact element 8a, and allows electrical contact to be provided from the outside to the first plate layer 4a, to define a first plate electrode A of the capacitive sensor 1.

Similarly, the capacitive sensor 1 comprises a second contact element 8b, made of conductive material, also copper for example, which extends vertically through the whole thickness of the second structural layer 5b, and which electrically contacts the second plate layer 4b, and in particular the plate of the detection capacitor C defined by the second plate layer 4b. A second contact opening 9b is formed through the lower metal layer 2b, at the position of the second contact element 8b, and allows electrical contact to be provided from the outside to the second plate layer 4b, to define a second plate electrode B of the capacitive sensor 1.

In the illustrated embodiment, the first and the second contact element 8a, 8b, as well as the first and the second contact opening 9a, 9b, have a circular cross section in the horizontal plane xy, the diameters of the circular cross sections of the contact openings 9a, 9b being greater than the respective diameters of the circular cross sections of the first and second contact element 8a, 8b. The aforesaid first and second contact element 8a, 8b are also positioned centrally relative to the whole structure of the capacitive sensor 1.

Figure 2:
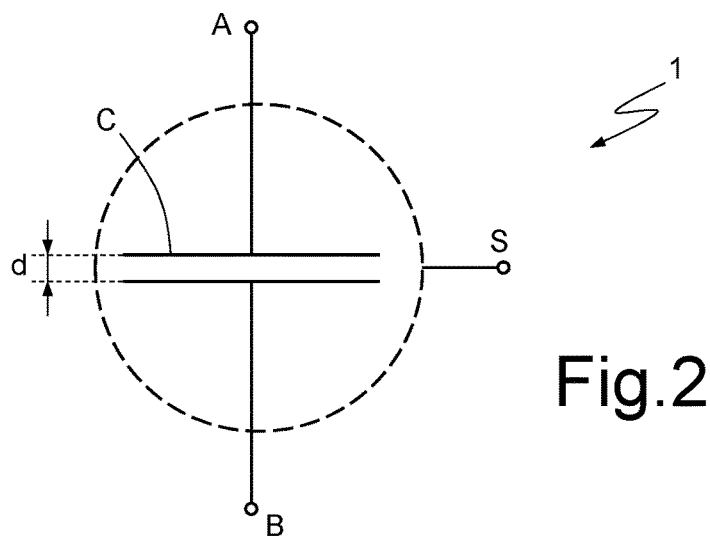
FIG. 2 is an equivalent electrical diagram of the capacitive pressure sensor of FIGS. 1A and 1B.

As also indicated in FIG. 2, which shows the equivalent circuit representation of the capacitive sensor 1, the same capacitive sensor 1 further comprises a screen electrode S, electrically contacting the upper metal layer 2a and the lower metal layer 2b, which jointly form an external screen to screen the capacitive sensor 1 against electromagnetic interference, thus insulating the interior of the capacitive sensor 1, and in particular the detection capacitor C, from the electromagnetic interference.

In use, the capacitive sensor 1 detects a pressure P acting on the capacitive sensor 1 in a normal direction (along the vertical axis z). This pressure P causes a variation of the distance d between the plates of the detection capacitor C, that is to say between the first and the second plate layer 4a, 4b, which in turn is due to a corresponding variation of the thickness of the dielectric layer 6. Consequently there is a variation in the capacitance of the detection capacitor C, indicative of the pressure P to be detected.

For example, if the pressure P creates a compressive stress, the thickness of the dielectric layer 6 decreases, as does the distance d between the first and the second plate layer 4a, 4b of the capacitive sensor 1.

The value of the dielectric constant of the dielectric layer 6, the resting value of the distance d, and/or the dimensions in the horizontal plane xy of the first and second plate layer 4a, 4b may be selected in a suitable manner in order to obtain a desired sensitivity of the capacitive sensor 1 in relation to the pressure P to be detected, and, in general, in relation to the stresses to be monitored.

In particular, the capacitive sensor 1 may be designed so as to be sensitive only to the normal component of the pressure P, while any horizontal component of the pressure P causes no appreciable variations in the capacitance of the detection capacitor C.

As indicated above, the upper metal layer 2a and the lower metal layer 2b may be connected by means of the screen electrode S to a suitable reference potential (such as an earth or ground potential), so as to form a screen against electromagnetic interference, for example interference generated by electrical machinery operating in the working environment of the capacitive sensor 1 (the screen forming a kind of Faraday cage in which the detection capacitor C is placed). Thus the operating state of the capacitive sensor 1 can also be monitored during the stages of installation, and rapid action can be taken, for example in case of breakage or malfunction.

According to a particular aspect of the present solution, as shown schematically in FIGS. 1A and 1B, the capacitive sensor 1 further comprises a suitable number of brackets or clamps 10, coupled to the upper metal layer 2a and/or to the lower metal layer 2b, outside the structure of the capacitive sensor 1.

Each bracket 10 has a coupling portion 10a, for coupling to the outer surface of the respective upper or lower metal layer 2a, 2b. A body portion 10b extending from the outer surface of the respective upper or lower metal layer 2a, 2b along the direction of the vertical axis z, and a head portion 10c, connected to the body portion 10b and extending transversely to the body portion 10b and to the vertical axis z, being for example substantially parallel to the horizontal plane xy.

The extension and shape in the horizontal plane xy of the coupling portion 10a of the brackets 10 may be of various types, for example circular or rectangular. Similarly, the shape of the body portion 10b may be of different types, for example in the form of a parallelepiped or a truncated pyramid or cone.

In the illustrated embodiment, the brackets 10 are coupled to the surface of the respective upper or lower metal layer 2a, 2b at corresponding lateral peripheral portions, for example at four lateral peripheral portions arranged substantially at the same distance from the geometric center of the upper or lower metal layer 2a, 2b in the horizontal plane xy.

Alternatively, as described below, a single bracket 10 may be provided, coupled in a suitable manner to the respective upper or lower metal layer 2a, 2b, for example in the center of the layer.

The presence of the brackets 10 enables the capacitive sensor 1 to be sensitive not only to compressive stresses generating a pressure P on the respective upper and lower metal layers 2a, 2b, but also to tensile stresses generating a counter-pressure P' on the upper and lower metal layers 2a, 2b (see FIG. 1B).

The brackets 10 also form suitable elements for the attachment or adhesion of the capacitive sensor 1 to the material of the structure to be monitored (concrete, for example), thereby reducing the risk of detachment or delamination.

In particular, the presence of the brackets 10 ensures that the capacitive sensor 1 operates correctly even in the presence of bubbles or other impurities (such as sand or grit) within the structure to be monitored.

Figure 3A:
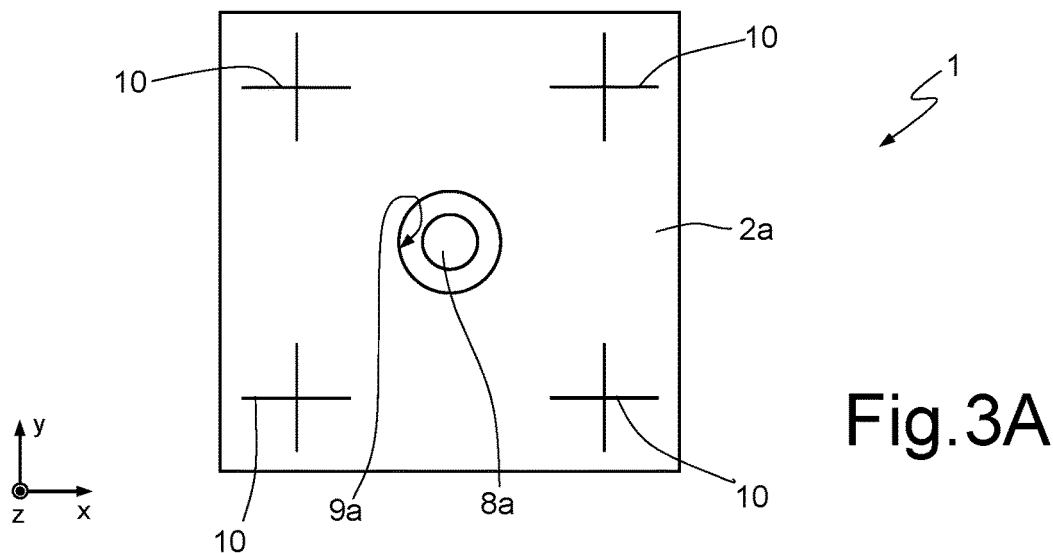
FIGS. 3A-3B are schematic top views of variant embodiments of the capacitive pressure sensors of the present disclosure.
Figure 3B:
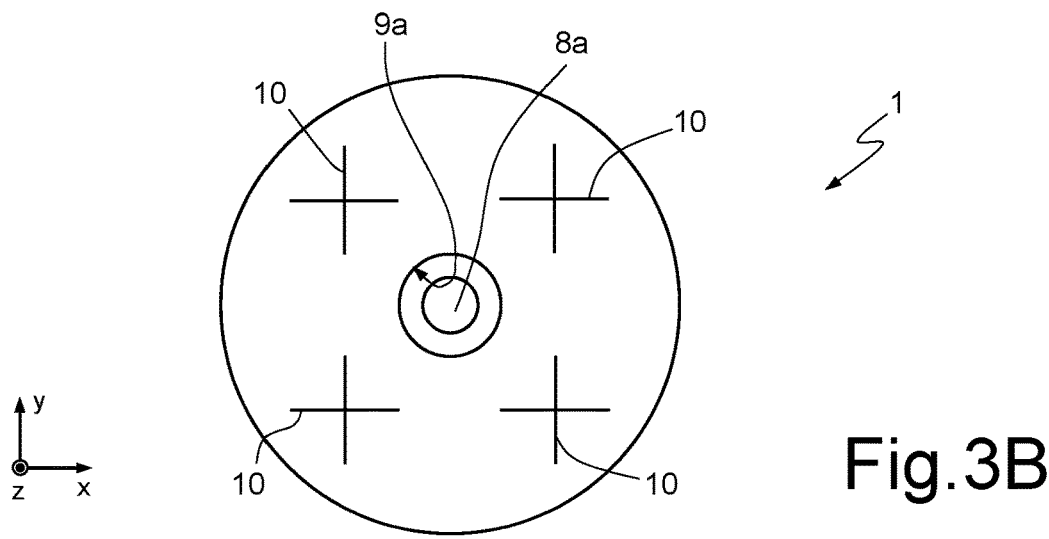

As shown in FIGS. 3A and 3B, the shape in the horizontal plane xy of the upper and lower metal layers 2a, 2b of the capacitive sensor 1 (and therefore the profile of the capacitive sensor 1 in the horizontal plane xy) may be square (FIG. 3A) or circular (FIG. 3B), for example, instead of rectangular (as shown in the aforesaid FIG. 1A).

Figure 4:
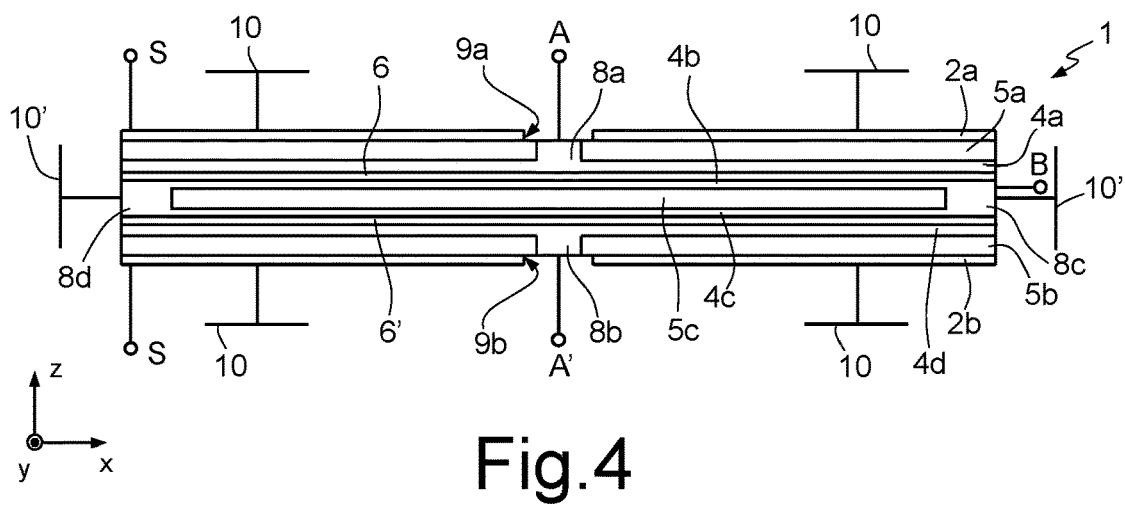
FIGS. 4-5 are cross-sectional views of further variants of capacitive pressure sensors according to embodiments of the present disclosure.

FIG. 4 shows a possible variant of the capacitive sensor 1, in which the corresponding stacked multi-layer structure comprises a larger number of stacked layers.

In particular, in this case the capacitive sensor 1 comprises a further dielectric layer 6', a third and a fourth plate layer 4c, 4d, and a third structural layer 5c. In this case, the second and third plate layer 4b, 4c are electrically connected to one another by means of lateral connecting elements 8c, 8d, so that they jointly form a central plate, and the third structural layer 5c is interposed between the second and third plate layer 4b, 4c, in the center of the multi-layer structure. The third and the fourth plate layer 4c, 4d, with the interposed further dielectric layer 6', form a further detection capacitor.

In this case, the lateral connecting elements 8c, 8d are electrically contacted by a further plate electrode, and are also coupled to further brackets 10', in this case extending laterally relative to the stacked structure of the capacitive sensor 1. The presence of these further brackets 10' ensures that the central plate of the capacitive sensor 1 is substantially fixed relative to the pressure P to be detected.

In this embodiment, the capacitive sensor 1 is capable of detecting not only the amount of pressure P acting in the direction of the vertical axis z, but also the direction of this pressure along the vertical axis z, or of determining whether the pressure is acting above or below the capacitive sensor 1 (given that, in this case, different variations in the capacitance of the detection capacitors occur, above and below the vertical axis z. It should be noted that, in this case, a respective plate electrode A' is provided for the electrical connection of the fourth plate layer 4d).

Figure 5:
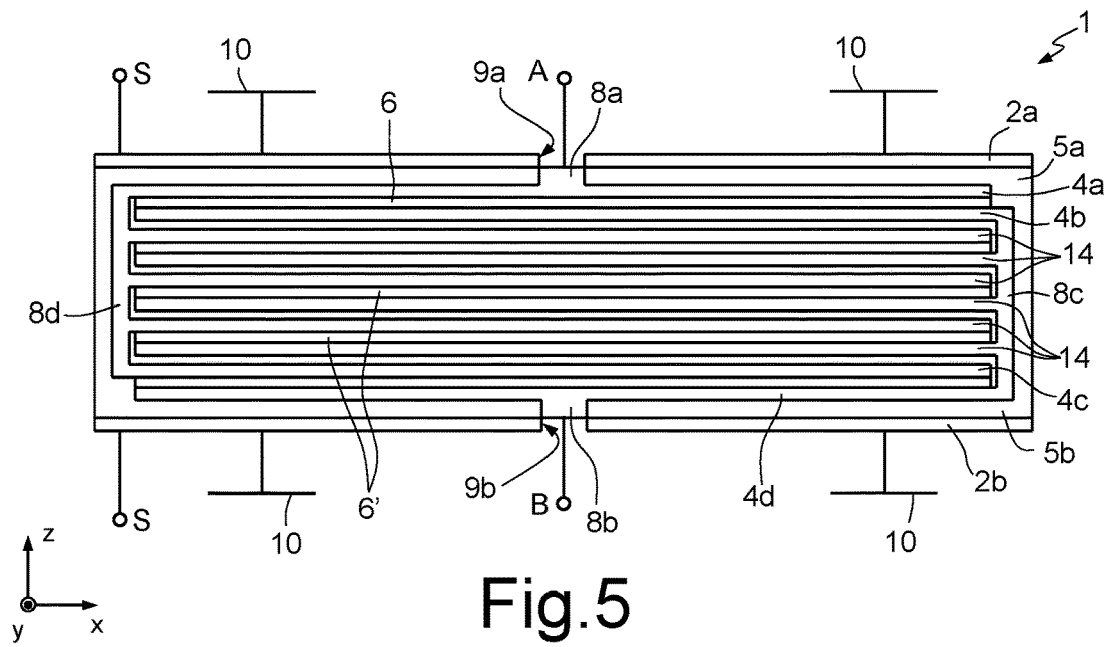

As shown in FIG. 5, the stacked structure of the capacitive sensor 1 may comprise an even greater number of stacked layers, and in particular further dielectric layers 6' and further plate layers, indicated here in general by 14, interposed and interleaved with one another to form further detection capacitors.

In the example shown in FIG. 5, the capacitive sensor 1 comprises five detection capacitors, formed by respective plate layers 4a-4d, 14 and dielectric layers 6, 6'. Additionally, in this example, the plate layers 4a-4d, 14 are alternately (along the direction of the vertical axis z) electrically connected to one another by respective lateral connecting elements 8c, 8d, so that the detection capacitors are connected in parallel with one another to form a single resulting detection capacitor C between the first and the second plate electrode A, B.

It will be evident, however, that different connections may be made, in series for example, among the detection capacitors. It may also be possible to provide different dielectric materials for the various dielectric layers 6, 6'.

With initial reference to FIGS. 6A and 6B-6C, a particular embodiment of the capacitive sensor 1 will now be described, this embodiment being especially suitable for monitoring a construction structure made of concrete, for example a tunnel, the capacitive sensor 1 in this example being intended to be embedded within an elementary structural element, for example a segment, of this construction structure.

In this embodiment, the capacitive sensor 1 is formed by the stacked superimposition of two double-faced multi-layer sheets, indicated by 15a, 15b, with the dielectric layer 6 interposed, in this case made of Kapton as a dielectric material (a material which advantageously has high thermal stability).

Each of these sheets 15a, 15b is formed by a core of insulating material, in this case FR-4, covered on both of the main outer faces (the upper and lower faces) by a conductive covering sheet or layer, in particular a layer of copper. For example, the thickness of this conductive covering layer is 35 μm, and the thickness of the whole sheet 15a, 15b is 1.6 mm (it should be noted that the drawings are plainly not to scale, in the interests of clarity of illustration).

The structure of the sheets 15a, 15b is therefore entirely similar to the structure of a double-faced printed circuit board (PCB). In this case, therefore, the methods for forming the capacitive sensor 1 may advantageously make use of common printed circuit board manufacturing methods, as will be evident to those skilled in the art. FR-4 has a Young's modulus of about 24 GPa and a maximum dielectric constant of 4.7 (this dielectric constant is, for example, 4.35 at a frequency of 500 MHz, and 4.34 at a frequency of 1 GHz), Kapton has a Young's modulus of about 2.5 GPa and a dielectric constant of 3.5 at a frequency of 1 kHz.

Figure 6A:
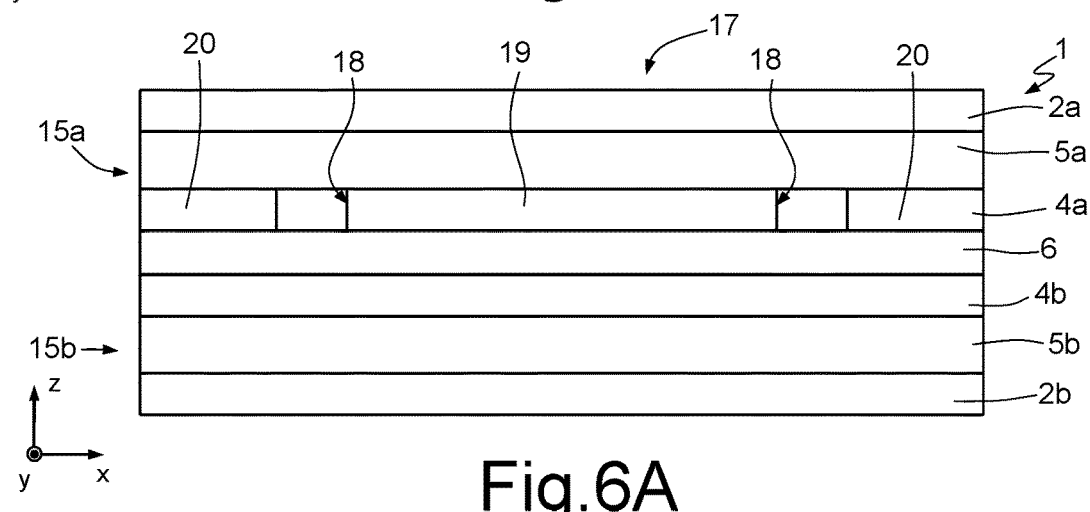
FIG. 6A is a cross-sectional view of a capacitive pressure sensor according to a further embodiment of the present solution.

In detail, as shown in FIG. 6A, a first sheet 15a, placed at the top in the stacked structure of the capacitive sensor 1, therefore defines the upper metal layer 2a, the first structural layer 5a and the first plate layer 4a. Similarly, the second sheet 15b, placed at the bottom in the stacked structure of the capacitive sensor 1, defines the lower metal layer 2b, the second structural layer 5b and the second plate layer 4b.

The dielectric layer 6 may have a thickness of between 25 and 100 μm, for example (it should be re-emphasized that the drawings are not to scale, in the interests of clarity of illustration). This dielectric layer 16 may, for example, be made in a modular manner, by superimposing a suitable number of Kapton sheets, each having a thickness of 25 μm.

In a manner which is not illustrated, it is also possible to provide filling and adhesion layers between the metal and dielectric layers, such layers being called "pre-preg" layers, as is well known from printed circuit board manufacturing technology.

Figures 6B, 6C:
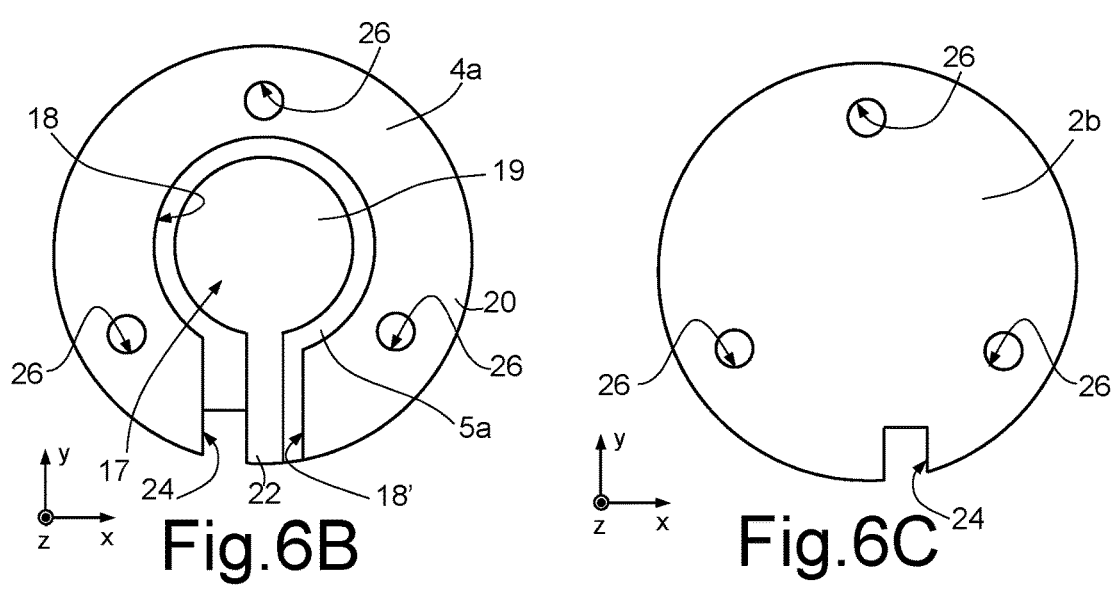
FIG. 6B is a layout view of a first plate layer of the sensor of FIG. 6A.
FIG. 6C is a layout view of a lower metal layer of the sensor of FIG. 6A.

According to an aspect of the present solution (reference should also be made to FIG. 6B, showing the layout of the first plate layer 4a, viewed in the direction of the upper metal layer 2a), the first plate layer 4a (carried by the first sheet 15a in this case) is suitably shaped so as to define an active area 17 of the capacitive sensor 1, that is to say the shape and size of a corresponding first plate of the detection capacitor C.

In particular, a first trench 18 is formed through the whole thickness of the first plate layer 4a (and through part of the first structural layer 5a if necessary) so as to define and separate an active portion 19 of the first plate layer 4a, inside the first trench 18 in the horizontal plane xy, from an outer portion 20 of the first plate layer 4a, positioned outside the first trench 18.

In the illustrated example, the first trench 18, which is internally empty, is substantially ring-shaped, and the active portion 19, defining the first plate of the detection capacitor C, has a substantially circular shape in the horizontal plane xy.

In the illustrated embodiment, the shape of the capacitive sensor 1 is also substantially circular in the horizontal plane xy. In particular, in the example, the diameter of the active portion 19 (that is to say, the plate of the detection capacitor C) may be between 20 and 26 mm, while the outside diameter of the whole structure of the capacitive sensor 1 may be between 37 and 47 mm (it should be noted that these dimensions are provided purely by way of example).

According to a further aspect of the present solution, the trench 18 has an extension portion 18', extending along a horizontal axis of the horizontal plane xy (along the y axis in the example), also defining an electrical connection portion 22 from the first plate layer 4a, this portion running from the active portion 19 and passing through the outer portion 20 of the first plate layer 4a, and extending, in the example, as far as an outer lateral edge of the first plate layer 4a and of the whole structure of the capacitive sensor.

As shown in FIG. 6C, an opening 24 is also formed through the upper metal layer 2a and through the first structural layer 5a, at the aforesaid outer lateral edge of the first plate layer 4a, so as to allow an electrical connection to be made, for example by means of an electrical wire placed laterally to the structure of the capacitive sensor 1, to the electrical connection portion 22 (and consequently to the active portion 19 of the first plate layer 4a and the corresponding first plate of the detection capacitor C). It should be noted that, in this case, the electrical connection portion 22 has a similar function to that of the contact element 8a defined above with reference to FIG. 1B, since it contributes to the definition of the first plate electrode A and allows the electrical connection to be made to the first plate of the detection capacitor C.

It will be evident that the electrical connection to the second plate of the detection capacitor C (formed by the second plate layer 4b) may, in this case, also be formed laterally to the structure of the capacitive sensor 1.

As shown in the FIGS. 6B and 6C, the capacitive sensor 1 further comprises fastening through holes 26, these holes being three in number in the example, which pass through the whole thickness of the multi-layer structure of the capacitive sensor 1. The inside of the fastening through holes 26 is conveniently plated, with copper for example.

The fastening through holes 26 may, for example, be placed at the vertices of a regular triangle inscribed in the outer portion 20 of the first plate layer 4a (and similarly through the other stacked layers).

Figure 7:
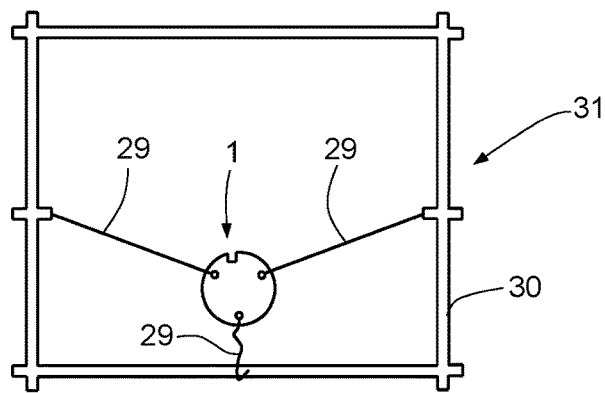
FIG. 7 is a schematic representation of a capacitive pressure sensor, fixed to a supporting structure, particularly a cage for concrete construction, according to an embodiment of the present disclosure.

As shown schematically in FIG. 7, tie wires 29 may be introduced through these fastening through holes 26, the tie wires being rigid and/or elastic or partially elastic, and usable for fastening or attaching the capacitive sensor 1 to external support or fastening structures 30, for example a cage consisting of tubes of iron or other material, made for the casting of the concrete and the production of a corresponding construction structure 31, for example a segment. The tie wires 29 advantageously enable the capacitive sensor 1 to be simply and stably positioned, when they are embedded in the construction structure 31.

Figure 8A:
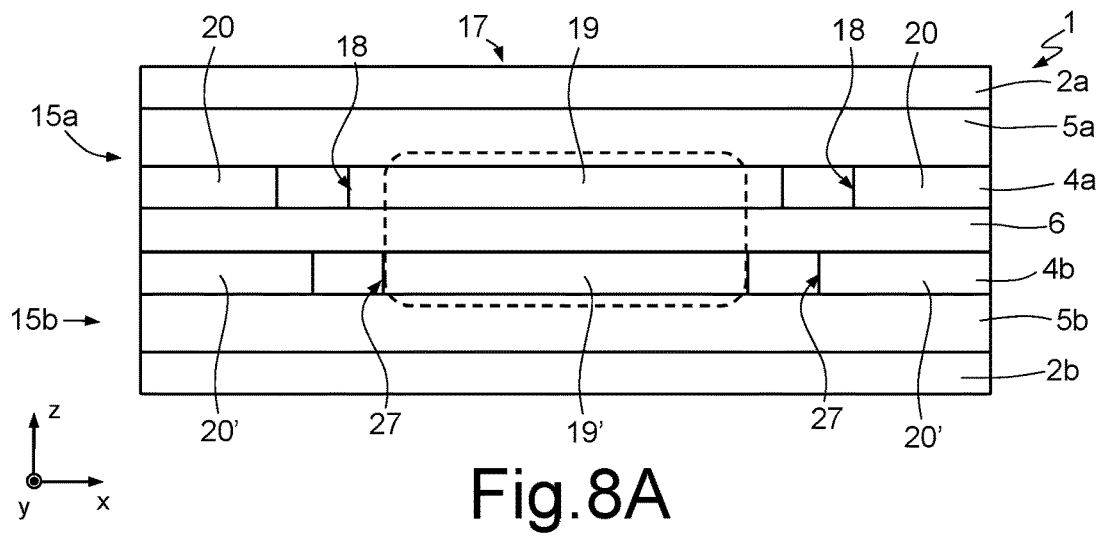
FIG. 8A is a cross-sectional view of a capacitive pressure sensor according to yet another embodiment of the present solution.

In a further embodiment, shown in FIGS. 8A (in cross section) and 8B-8E (which show the layout of the upper metal layer 2a, the first plate layer 4a, the second plate layer 4b and the lower metal layer 2b, respectively), of the capacitive sensor 1, the second plate layer 4b carried by the second sheet 15b is also suitably shaped so as to define the active area 17 of the capacitive sensor 1, that is to say the shape and size of a corresponding second plate of the detection capacitor C.

In particular (see FIG. 8D), a second trench 27 is formed through the whole thickness of the second plate layer 4b (and through part of the second structural layer 5b if necessary) so as to define and separate an active portion 19' of the second plate layer 4b, inside the second trench 27 in the horizontal plane xy, from an outer portion 20' of the second plate layer 4b, positioned outside the second trench 27.

In the illustrated example, the second trench 27 is substantially ring-shaped, and the active portion 19', defining a corresponding second plate of the detection capacitor C, has a substantially circular shape in the horizontal plane xy.

In particular, the diameter of the active portion 19' defined in the second plate layer 4b, which, purely by way of example, is equal to 10 mm, is in this case smaller than the diameter of the corresponding active portion 19 defined in the first plate layer 4a, which, purely by way of example, is equal to 11 mm. The dimensions of the effective capacitive detection area (indicated by the box drawn in broken lines in FIG. 8A) are therefore defined in this case by the dimensions of the active portion 19' of the second plate layer 4b.

Advantageously, this characteristic of superimposition (or "overlap") between the active portions 19, 19' causes the capacitive sensor 1 to be entirely insensitive to transverse components of the pressure P to be monitored, acting in a direction lying in the horizontal plane xy. In fact, stresses acting in this direction, even if they cause a relative movement between the two plates of the detection capacitor C, are not in any case capable of altering the dimensions of the effective detection area, which continues to be determined by the smaller of the two plates (as is also shown by the aforesaid box drawn in broken lines in FIG. 8A). Similarly, this solution can ensure that any errors of misalignment between the layers that may occur during the manufacture of the capacitive sensor 1 have no effect.

As shown schematically in FIG. 9, the presence of the trenches 18, 27 in both plate layers 4a, 4b causes the electric field lines E at the edges of the detection capacitor C to be entirely closed through the dielectric layer 6 and the outer portion 20, 20' of the plate layers 4a, 4b, and in any case within the structure of the capacitive sensor 1, instead of passing out into the environment outside the capacitive sensor 1, that is to say into the material of the structure to be monitored (for example concrete, whose precise dielectric characteristics are not known, which characteristics may depend, among other things, on the composition and on the moisture that may be present in such material).

As shown in the FIG. 9, the capacitive sensor 1 may if necessary have an insulating coating 32, made of silicone for example, covering the whole outer lateral surface of the multi-layer structure of the capacitive sensor 1, thus further improving the insulation and impermeability characteristics of the capacitive sensor 1 in relation to the moisture and other factors that may be present in the environment outside the capacitive sensor 1.

As shown in FIG. 8D, the second trench 27 also has an extension portion 27', extending along a horizontal axis of the horizontal plane xy (along the y axis in the example), defining a respective electrical connection portion 22' from the second plate layer 4b, which portion runs from the active portion 19' and reaches the outer portion 20' of the second plate layer 4b, to allow the electrical connection to be provided from the outer lateral surface of the capacitive sensor 1 (defining the second plate electrode B).

Figures 8B, 8C:
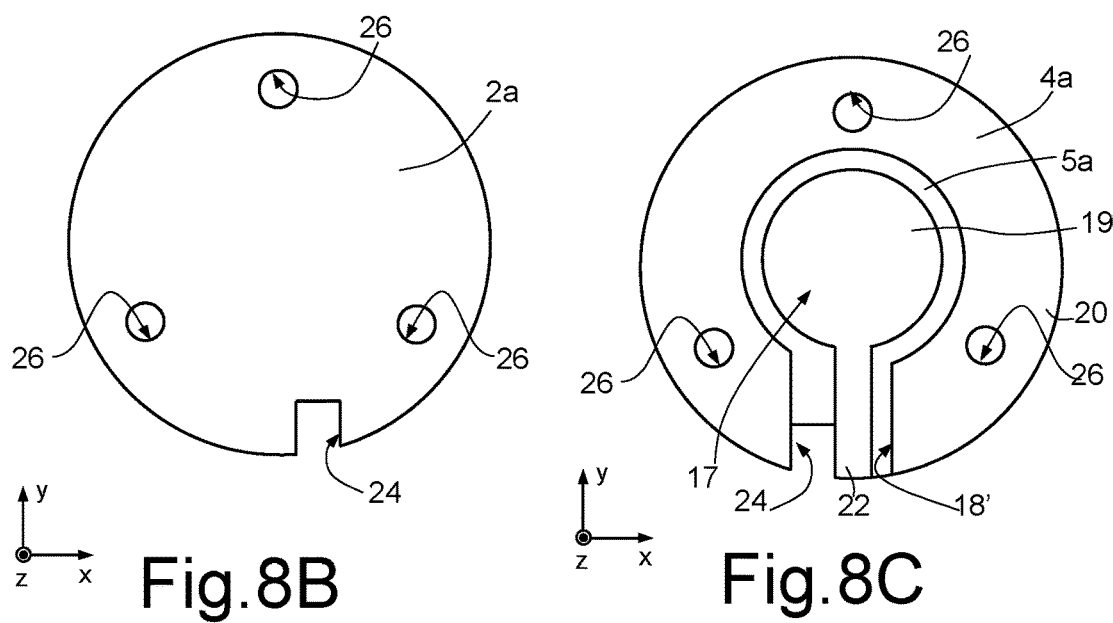
FIG. 8B is a layout view of an upper metal layer of the sensor of FIG. 8A.
FIG. 8C is a layout view of a first plate layer of the sensor of FIG. 8A.

As also shown in FIGS. 8B, 8E, the upper and lower metal layers 2a, 2b, as well as the first and second structural layer 5a, 5b, may have corresponding openings 24 for the lateral access of the electrical connection wires to the plates of the detection capacitor C.

In detail, the solution described here may advantageously allow some variants of the electrical connection to the plates of the detection capacitor C, via the first and second plate electrode A, B and the screen electrode S.

In a first variant, shown schematically in FIG. 10A, the measurement of capacitance, made by a suitable measurement circuit 35 supplied with a power supply voltage $V_{cc}$, is insulated or differential, that is to say made between the two plates of the detection capacitor C, both biased to a voltage other than the ground potential gnd of the measurement circuit 35. The first and second plate electrode A, B are therefore insulated from the ground gnd and each connected to a respective pole of an electrical connecting cable. The screen electrode S of the capacitive sensor 1 is, in this case, connectable to the ground potential gnd, or, as in the illustrated example, to an earth potential, coinciding with the earth screen 36 of an electronic apparatus 37 of which the measurement circuit 35 forms a part.

Figure 10B:
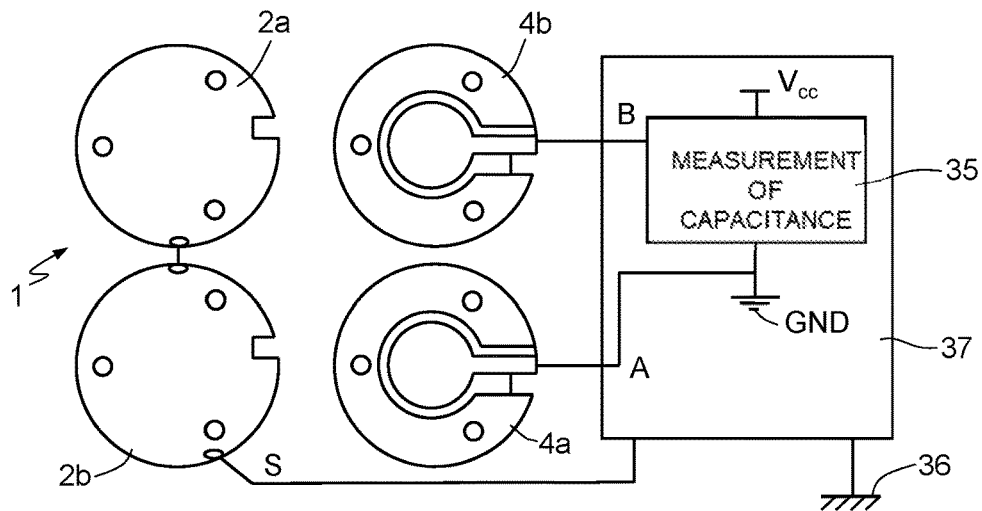

In a second variant, shown schematically in FIG. 10B, the measurement of capacitance is unipolar or relative to earth, that is to say, one of the two plates of the detection capacitor C is connected to the ground potential gnd of the circuit. In the example, the first plate electrode A is connected to the ground gnd, while the second plate electrode B is connected to a single pole of an electrical connecting cable. In this case also, the screen electrode S of the capacitive sensor 1 is connectable to the ground potential gnd, that is to say to the earth screen 36 of the electronic apparatus 37.

Figure 11A:
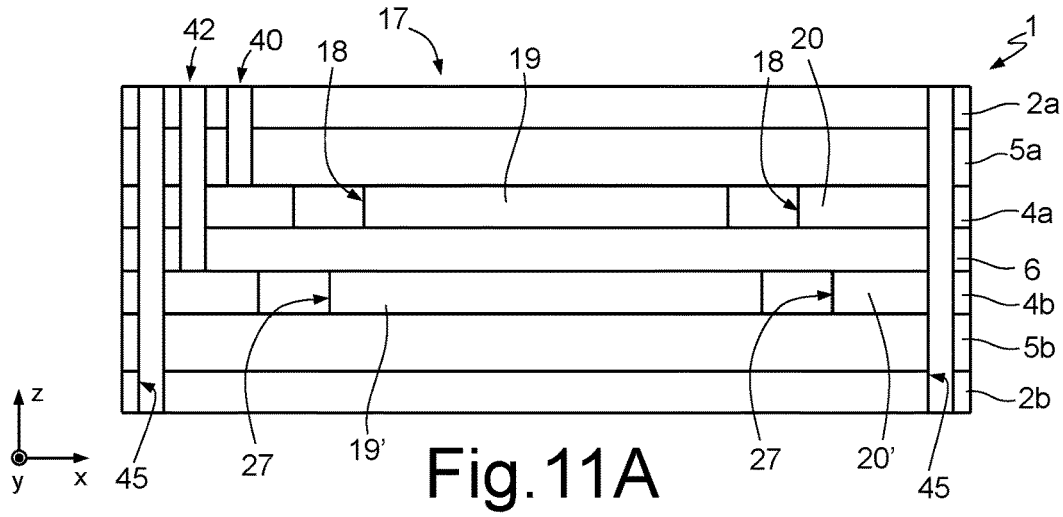
FIG. 11A is a cross-sectional view of a capacitive pressure sensor according to yet another embodiment of the present solution.
Figure 11B:
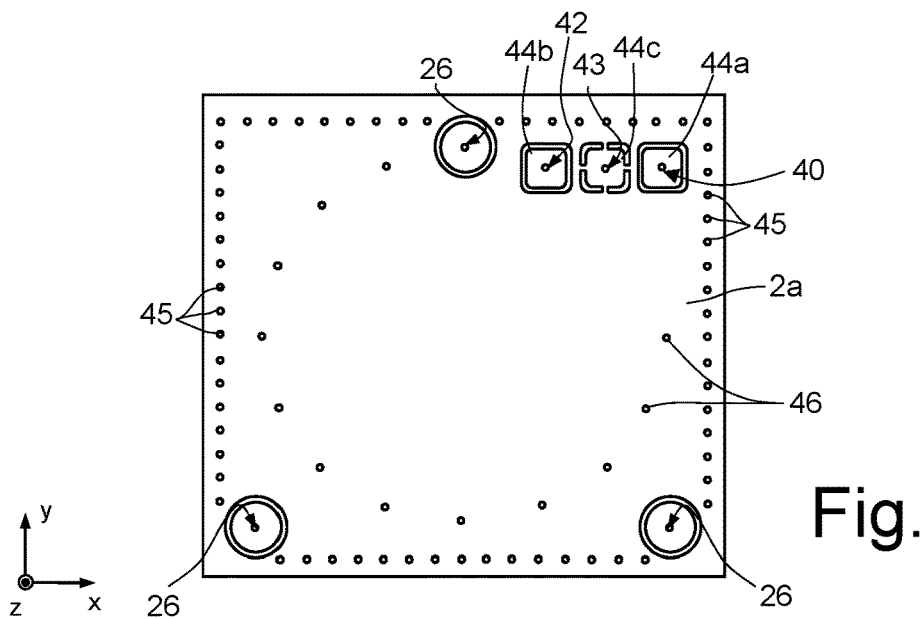
FIG. 11B is a layout view of an upper metal layer of the sensor of FIG. 11A.
Figure 11C:
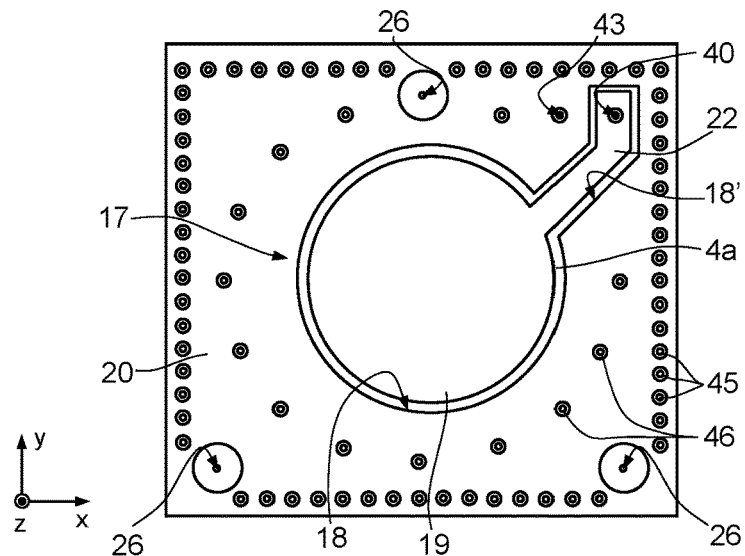
FIG. 11C is a layout view of a first plate layer of the sensor of FIG. 11A.
Figure 11D:
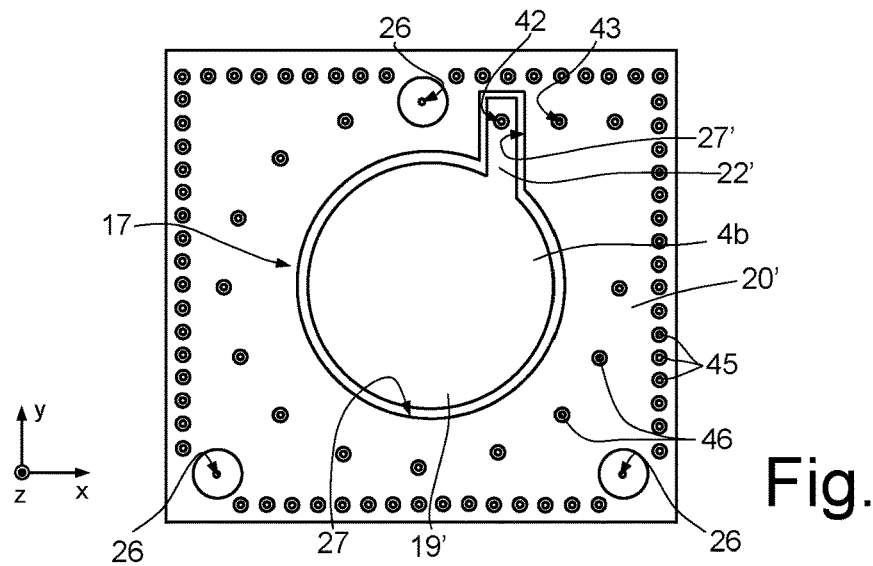
FIG. 11D is a layout view of a second plate layer of the sensor of FIG. 11A.
Figure 11E:
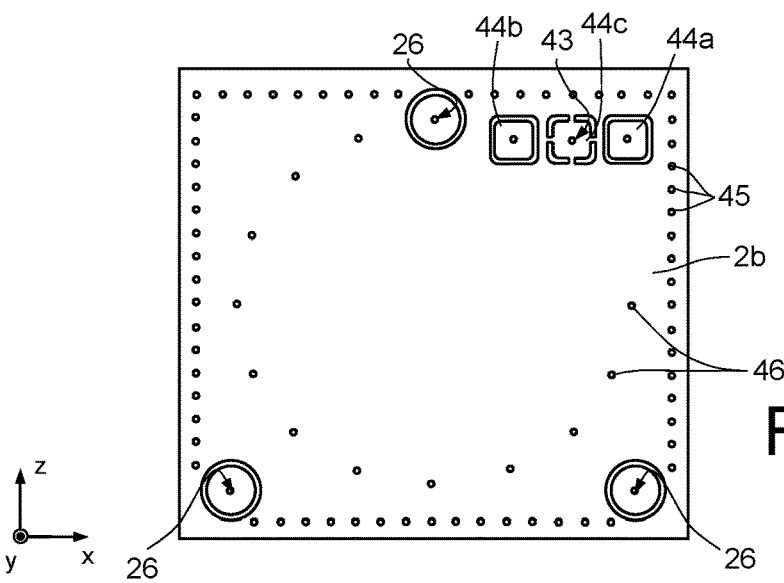
FIG. 11E is a layout view of a lower metal layer of the sensor of FIG. 11A.

Yet another embodiment of the capacitive sensor 1 will now be illustrated with reference to FIGS. 11A (in cross section) and 11B-11E (which show the layout of the upper metal layer 2a, the first plate layer 4a, the second plate layer 4b and the lower metal layer 2b, respectively).

This embodiment differs from that illustrated above in that the electrical connection to the plates of the detection capacitor C is provided from a peripheral edge portion of the upper surface of the upper metal layer 2a (and/or of the lower surface of the lower metal layer 2b) of the capacitive sensor 1, outside the active area 17 of the capacitive sensor 1 (which in this case has a square or rectangular profile), instead of the provision of a lateral access for the electrical connecting wires.

In this case, a first connecting hole 40 (also called a "via") is provided, this hole being plated on its inner wall (and insulated externally from the layers of the structure through which it passes). It runs, for example, from the upper surface of the upper metal layer 2a, passes through the upper metal layer 2a and the first structural layer 5a, and reaches the first plate layer 4a, where it terminates at the electrical connection portion 22, outside the active portion 19 of this first plate layer 4a. This electrical connection portion 22, as discussed above, reaches the active portion 19 of the outer portion 20 by following a suitable route through the first plate layer 4a.

Similarly, a second connecting hole 42 is provided. It also runs, for example, from the upper surface of the upper metal layer 2a, passes through the upper metal layer 2a, the first structural layer 5a, the first plate layer 4a and the dielectric layer 6, and reaches the second plate layer 4b, where it terminates at the respective electrical connection portion 22', outside the active portion 19' of this second plate layer 4b. The electrical connection portion 22', as discussed above, reaches the respective active portion 19' of the second plate layer 4b by following a suitable route from the outer portion 20'.

A first and a second electrical contact pad 44a, 44b are provided on the aforesaid peripheral edge portion of the upper metal layer 2a, to allow electrical connections to be made to the plates of the detection capacitor C, thus defining the first and second plate electrode A, B.

If necessary (as illustrated in FIGS. 11B-11E, but not in FIG. 11A), the aforesaid first and second connecting hole 40, 42 may continue through the remaining layers of the structure of the capacitive sensor 1, until they reach the lower surface of the lower metal layer 2b, where further electrical contact pads may be provided for making additional electrical connections to the plates of the detection capacitor C from the lower surface of the capacitive sensor 1.

A third electrical contact pad 44c is also provided, in a position adjacent to the aforesaid first and second electrical contact pad 44a, 44b, to define the screen electrode S of the capacitive sensor 1.

A screen hole 43 (not shown in FIG. 11A) is also provided, and is also plated on its inner wall (and externally insulated), this hole passing through the whole structure of the capacitive sensor 1, from the upper surface of the upper metal layer 2a to the lower surface of the lower metal layer 2b, where a further electrical contact pad may be provided if necessary, for electrical connection to the screen of the capacitive sensor 1.

In the illustrated embodiment, there are also plated through holes 45, which also pass through the whole structure of the capacitive sensor 1, and are positioned with uniform spacing along the whole lateral perimeter of the capacitive sensor 1. These plated through holes 45 jointly define a further screen against electromagnetic interference, this screen also laterally insulating and screening the detection capacitor C formed inside the structure of the capacitive sensor 1.

In this embodiment also, the fastening through holes 26, which may advantageously also be internally plated, are provided.

Further through holes 46 may also be provided, these holes being, for example, distributed uniformly outside the active area 17 of the capacitive sensor 1 and having the same cross section as, or a larger cross section than, the plated through holes 45. Advantageously, these further through holes 46, being internally plated, may contribute to the definition of the electrostatic screen, as well as to the mechanical locking between the layers of the sensor (by means of the corresponding internal plating).

Figure 12:
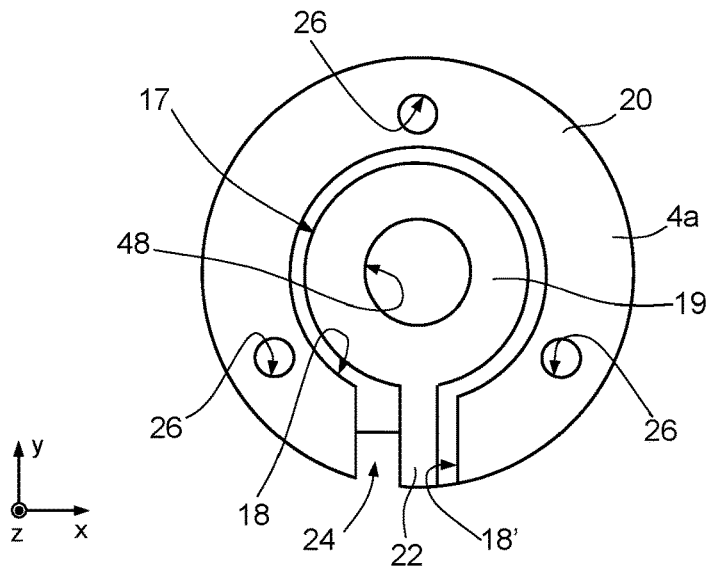
FIG. 12 is a layout view of a plate layer of a further variant of a capacitive pressure sensor according to an embodiment of the present disclosure.

In a possible variant, shown schematically in FIG. 12, one or more through holes 48 may if necessary also be provided in the active area 17 of the capacitive sensor 1. The example shows a single through hole 48, which passes centrally through the plate of the detection capacitor C defined by the active portion 17 of the first plate layer 4a (having a resulting circular ring shape in the horizontal plane xy, in this case).

These through holes 48, being capable of allowing fluid communication between the upper surface and the lower surface of the capacitive sensor 1, may advantageously allow the passage of air and thus prevent the formation of air bubbles that might adhere to the upper and lower surfaces of the capacitive sensor 1 and therefore impede the correct detection of the pressure P to be monitored.

One skilled in the art will appreciate that in all the embodiments of the capacitive sensor 1, the brackets 10, having the function illustrated above, may advantageously be provided (even where, in the interests of simplicity and clarity of illustration, this is not explicitly illustrated).

Figure 13A:
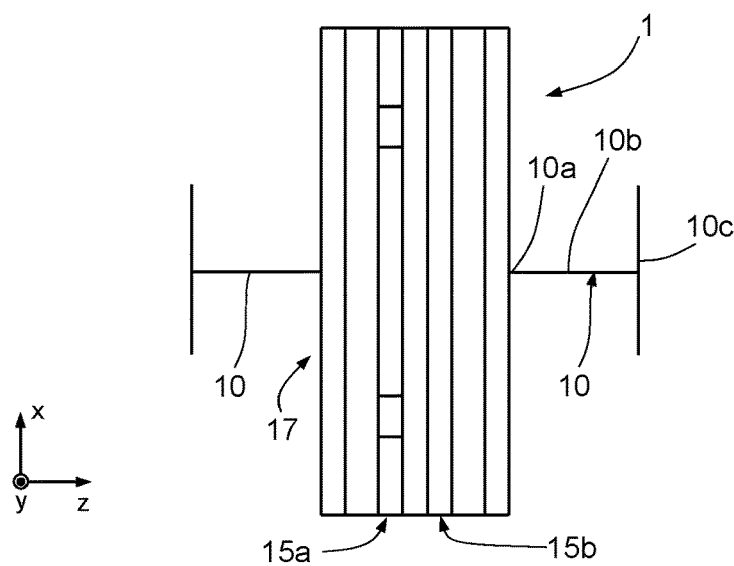
FIGS. 13A-13B are cross-sectional views of yet further variants of the capacitive pressure sensor according to an embodiment of the present disclosure.

For example, as shown schematically in FIG. 13A, only two brackets 10 may be provided, these brackets being positioned centrally, one on each upper and lower surface of the capacitive sensor 1, and coupled, respectively, to the upper metal layer 2a and the lower metal layer 2b.

As shown in the example, these brackets 10 may have a body portion 10b of parallelepipedal or trapezoidal shape.

Figure 13B:
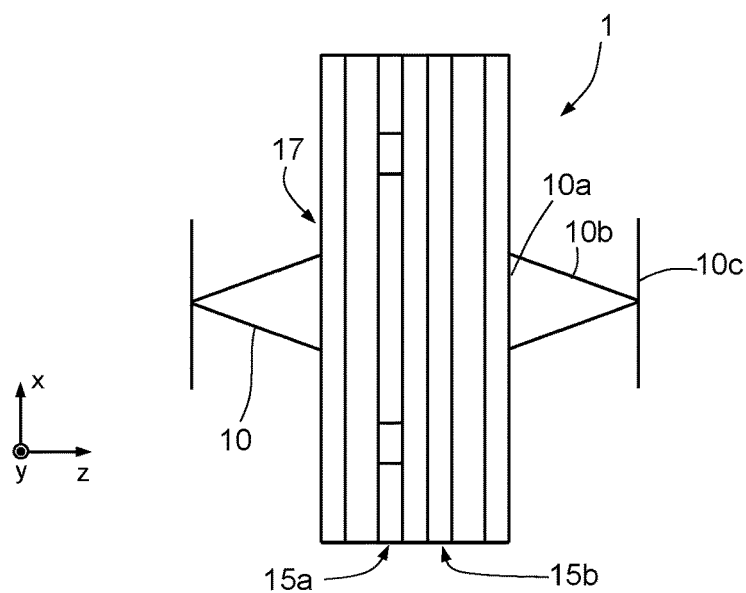

Alternatively, as shown schematically in FIG. 13B, the body portion 10b of the brackets 10 may be pyramidal or conical in shape (thereby providing a larger surface for coupling to the respective upper or lower metal layer 2a, 2b, on the corresponding coupling portion 10a).

Figure 14A:
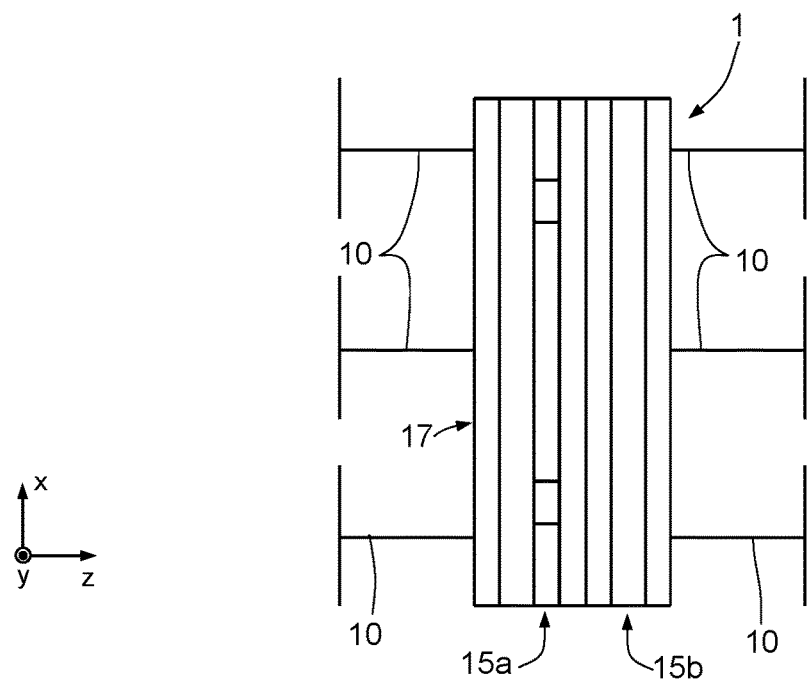
FIG. 14A is a cross-sectional view of a further variant of the capacitive pressure sensor according to an embodiment of the present disclosure.
Figure 14B:
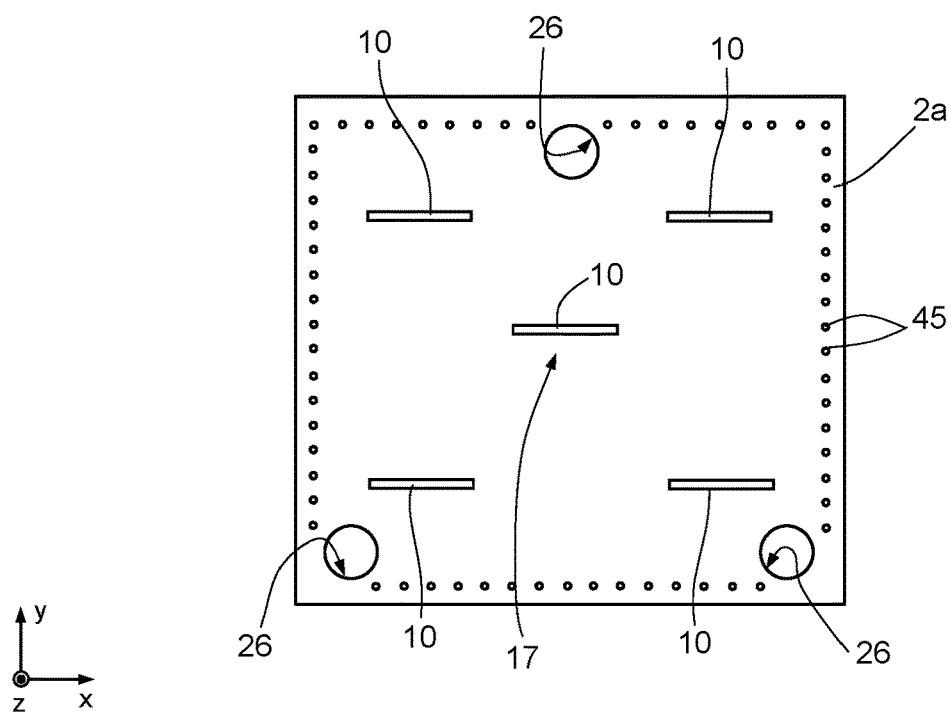
FIG. 14B is a schematic plan view of the sensor of FIG. 14A.

As shown in FIG. 14A (in cross section) and 14B (showing the layout of the upper metal layer 2a, or, similarly, of the lower metal layer 2b), various brackets 10 may be provided for each upper and lower surface of the capacitive sensor 1. In the example, four brackets 10 are provided, positioned on the periphery of the active area 17 of the capacitive sensor 1, as well as one bracket 10 positioned centrally in the active area 17 of the capacitive sensor 1.

The advantages of the described solution are evident from the preceding description.

In any case, it should be re-emphasized that this solution makes it possible to produce sensors, applied for example to buildings and civil engineering structures, which are capable of meeting one or more of the following requirements: high measurement accuracy; high robustness; low cost; high immunity to electromagnetic interference that might falsify the detection results; simplicity and stability of positioning; simplicity of operation; and good surface adhesion to the structure to be monitored.

Experimental tests and trials conducted by the applicant have demonstrated the accuracy of the measurements provided by the capacitive sensor 1, in real conditions of use, for monitoring active stresses that may reach high values of the order of hundreds of atmospheres (with an operating range up to a limit of 500 atm, for example).

Figure 15:
FIG. 15 shows graphs of electrical quantities associated with the capacitive pressure sensor according to an embodiment of the present disclosure.

For example, FIG. 15 shows a graph of the pressure values detected by the capacitive sensor 1, which in this case is embedded in a concrete segment in a detection time interval T. The corresponding values of capacitance of the detection capacitor C are also shown.

As shown by the graph, the values detected by the capacitive sensor 1 (shown by a solid line) reproduce, with a high level of accuracy, the theoretical or expected values (shown by a broken line). In particular, as indicated in the portions of the graph in the circular frames, the capacitive sensor 1 is also advantageously capable of detecting negative pressure values, if there are counter-pressure stresses acting in the monitored structure.

Additionally, as mentioned above, the capacitive sensor 1 may advantageously be produced by printed circuit board (PCB) manufacturing technology. The manufacture of the sensor is therefore fast and economical.

Figure 16:
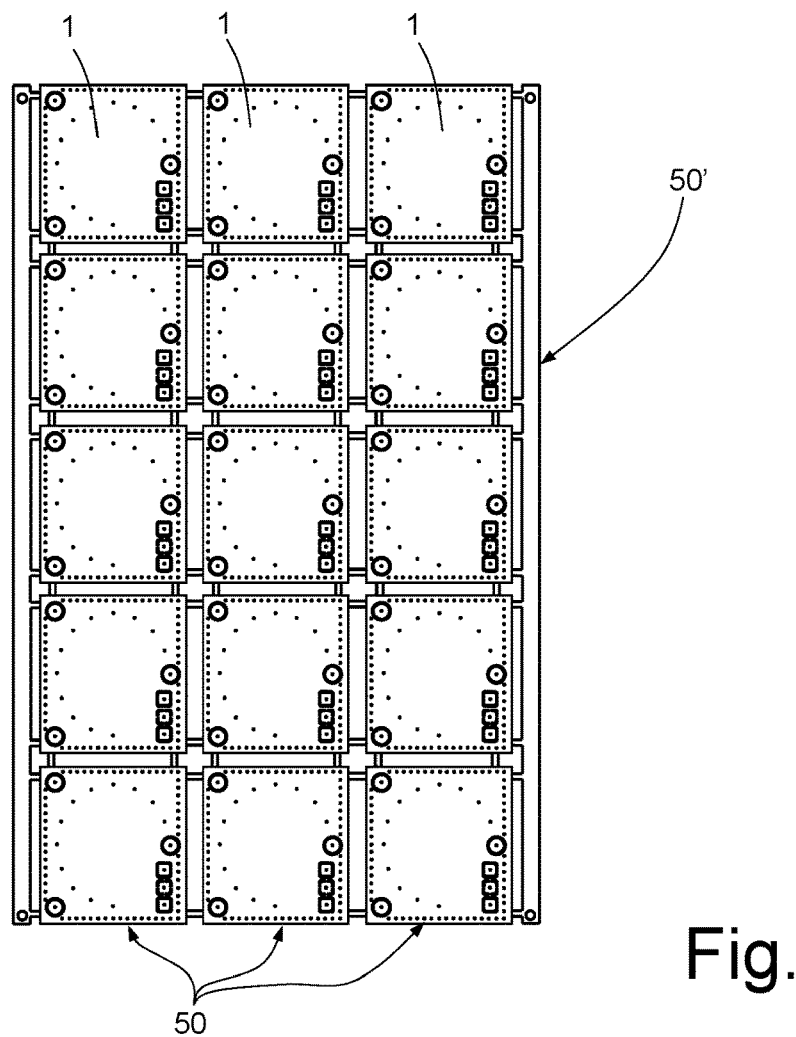
FIG. 16 shows a plan view of a set of elementary units of the capacitive pressure sensors according to embodiments of the present disclosure, according to a further aspect of the present solution.

On this subject, FIG. 16 shows, by way of example, a complete plate layer 50' including a plurality of elementary units 50 of the capacitive sensor 1, as a starting point from which the various elementary units 50 may be separated from one another to produce a corresponding capacitive sensor 1.

Finally, the solution described and illustrated herein can evidently be modified and varied without departure from the protective scope of the present disclosure, as defined in the attached claims.

For example, the materials used to produce the capacitive sensor 1 could differ from those illustrated above. Similarly, further variant shapes could be provided for the structure of the capacitive sensor 1.

In particular, the materials forming the structural layer of the sheets 15a, 15b and the dielectric layer 6 could differ from those mentioned, namely FR-4 and Kapton, since suitable dielectric materials may also be used, provided that they satisfy the following condition:

$$E_C \geq E_P \geq E_D,$$

where $E_P$ denotes the value of the Young's modulus of the material forming the structural layer of the sheets 15a, 15b (FR-4 in the illustrated example); $E_D$ denotes the value of the Young's modulus of the material forming the dielectric layer 6 (Kapton in the illustrated example); and $E_C$ denotes the Young's modulus of the material of the structure to be monitored, which is concrete in the example, having a typical Young's modulus of 30 GPa.

It is also useful if the following further relations are satisfied:

$$\frac{E_C}{E_P} = \alpha$$

$$\frac{E_P}{E_D} = \beta$$

where α is a factor of proportionality, in the range from 1 to 2 for example, being equal to 1.25 for example; and β is a respective factor of proportionality in the range from 8 to 11, being equal to 9.6 for example.

It is also emphasized that one or more capacitive sensors 1 may advantageously be used even in existing structures, for monitoring the stresses acting in these structures, for example by making cuts or holes for the insertion of the capacitive sensors 1 into the structures.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A capacitive sensor, comprising:
    a multi-layer structure including:
        an upper conductive layer defining an upper outer surface of said sensor;
        a lower conductive layer defining a lower outer surface of said sensor, said upper conductive layer and said lower conductive layer configured to jointly define an electromagnetic screen for screening said detection capacitor against electromagnetic interference originating from outside said capacitive sensor;
        at least a first structural layer of insulating material in contact with said upper conductive layer;
        at least a second structural layer of insulating material in contact with said lower conductive layer;
        at least a first plate layer, of conductive material;
        at least a second plate layer of conductive material; and
        at least one dielectric layer interposed between said first plate layer and said second plate layer to define at least one detection capacitor inside the multi-layer structure of said capacitive sensor.

2. The sensor according to claim 1, wherein said multi-layer structure comprises at least a first and a second double-faced sheet, said first double-faced sheet defining the upper conductive layer, the first structural layer and the first plate layer and said second double-faced sheet defining the lower conductive layer, the second structural layer and the second plate layer, in the multi-layer structure of said capacitive sensor.

3. The sensor according to claim 2, wherein materials forming said first and second structural layer and said dielectric layer satisfy the following relation:

$$E_C \geq E_P \geq E_D,$$

where $E_P$ denotes the value of the Young's modulus of the material forming said first and second structural layer; $E_D$ denotes the value of the Young's modulus of the material forming said dielectric layer; and $E_C$ denotes the Young's modulus of a material of a construction structure in which said capacitive sensor is configured to be embedded.

4. The sensor according to claim 3, wherein the following further relations are also satisfied:

$$\frac{E_C}{E_P} = \alpha$$

$$\frac{E_P}{E_D} = \beta$$

where α is a factor of proportionality, in the range from 1 to 2, and β is a respective factor of proportionality in the range from 8 to 11.

5. The sensor according to claim 1, wherein each of said first and second structural layer is FR-4, and said dielectric layer is Kapton.

6. The sensor according to claim 1, further comprising:
    a number of brackets coupled to at least one of said upper conductive layer or said lower conductive layer outside the multi-layer structure of said capacitive sensor, wherein each bracket has a coupling portion configured to couple to a surface of the respective upper or lower conductive layer;
    a body portion extending from said surface of the respective upper or lower conductive layer transversely to this surface; and
    a head portion, connected to the body portion and extending transversely to said body portion and substantially parallel to the surface of the respective upper or lower conductive layer.

7. The sensor according to claim 6, wherein a shape of the body portion of said brackets is a parallelepipedal; trapezoidal; truncated pyramidal; or truncated conical.

8. The sensor according to claim 6, wherein said brackets are configured to allow the detection of tensile stresses generating a counter-pressure on said upper and lower conductive layers.

9. The sensor according to claim 6, also comprising brackets coupled laterally to said multi-layer structure and transversely to a vertical direction of stacking of said multi-layer structure.

10. The sensor according to claim 1, comprising a first trench formed through at least the whole thickness of said first plate layer to define and separate an active portion of said first plate layer inside the first trench, and to define a first plate of said detection capacitor from an outer portion of said first plate layer positioned outside said first trench.

11. The sensor according to claim 10, further comprising a second trench formed through at least the whole thickness of said second plate layer to define and separate an active portion of said second plate layer inside the second trench, and to define a second plate of said detection capacitor from an outer portion of said second plate layer positioned outside said second trench; said active portions of said first and second plate layer jointly defining an active detection area of said sensor.

12. The sensor according to claim 11, wherein a dimension of said first plate of said detection capacitor in a horizontal plane of main extension of said first plate layer is smaller than a corresponding dimension of said second plate of said detection capacitor in said horizontal plane.

13. The sensor according to claim 12, wherein said active detection area and the corresponding detection capacitor are capable of detecting a component of a pressure acting on the upper outer surface of said upper conductive layer and/or on the surface of said lower conductive layer of said capacitive sensor along a direction orthogonal to said surface, the sensor being insensitive to a component of said pressure parallel to said upper and lower outer surfaces.

14. The sensor according to claim 11, wherein said first and second trench each have a respective extension portion which defines, in the first and second plate layers, respectively, a respective electrical connection portion, which runs from the active portion and reaches the outer portion of the first and second plate layers, respectively, the sensor further including electrical connecting elements for connection to said respective electrical connection portions configured to define a first and a second plate electrode of said detection capacitor.

15. The sensor according to claim 14, wherein said electrical connecting elements comprise a respective connecting hole plated on an internal wall which runs from the surface of the upper and/or lower conductive layer, and passes at least partially through said multi-layer structure of said capacitive sensor and reaches the first and the second plate layer respectively, terminating at the electrical connection portion outside the active portion of said first and second plate layer respectively.

16. The sensor according to claim 15, wherein said connecting elements further comprise a first and a second electrical contact pad on said surface of at least one of the upper or lower conductive layers in electrical contact with said connecting holes to allow electrical connections to be made to the plates of the detection capacitor to define said first and second plate electrode; wherein a third electrical contact pad is also provided in a position adjacent to said first and second electrical contact pad, and in electrical contact with said upper and lower conductive layer to define a screen electrode of said capacitive sensor.

17. The sensor according to claim 11, further comprising through holes passing through the whole thickness of said multi-layer structure and configured to allow fluid communication between the upper outer face and the lower outer face of said capacitive sensor.

18. The sensor according to claim 11, further comprising plated through holes which pass through the whole thickness of said multi-layer structure and are positioned along a lateral perimeter of the multi-layer structure of said capacitive sensor; said plated through holes jointly defining a screen against electromagnetic interference, which is configured to laterally insulate and screen the detection capacitor formed inside said multi-layer structure of said capacitive sensor.

19. The sensor according to claim 11, further comprising fastening through holes which pass through the whole thickness of the multi-layer structure of said capacitive sensor, and are positioned outside the active detection area, the fastening through holes configured to be engaged by rigid and/or elastic or partially elastic tie wires to a construction structure.

20. The sensor according to claim 1, also comprising further dielectric layers and further plate layers, configured to define at least one further detection capacitor configured to interact with said detection capacitor for detecting said stresses.

21. A stress detection system, comprising the capacitive sensor according to claim 1, and an electronic measurement circuit, coupled for operation to the capacitive sensor for processing corresponding detection signals indicative of said stresses.

* * * * *